(12) United States Patent
Chakraborty et al.

(10) Patent No.: US 9,988,488 B2
(45) Date of Patent: Jun. 5, 2018

(54) CATALYST FOR POLY(LACTIDE) SYNTHESIS AND USES THEREOF

(71) Applicant: INDIAN INSTITUTE OF TECHNOLOGY MADRAS, Chennai, Tamilnadu (IN)

(72) Inventors: Debashis Chakraborty, Tamilnadu (IN); Swarup Ghosh, Tamilnadu (IN); Venkatachalam Ramkumar, Tamilnadu (IN)

(73) Assignee: INDIAN INSTITUTE OF TECHNOLOGY MADRAS, Tamil Nadu (IN)

( * ) Notice: Subject to any disclaimer, the term of this patent is extended or adjusted under 35 U.S.C. 154(b) by 0 days. days.

(21) Appl. No.: 14/781,016

(22) PCT Filed: Mar. 3, 2014

(86) PCT No.: PCT/IB2014/059377
§ 371 (c)(1),
(2) Date: Sep. 28, 2015

(87) PCT Pub. No.: WO2014/155213
PCT Pub. Date: Oct. 2, 2014

(65) Prior Publication Data
US 2016/0053048 A1    Feb. 25, 2016

(30) Foreign Application Priority Data
Mar. 26, 2013  (IN) .......................... 1338/CHE/2013

(51) Int. Cl.
*C07F 5/06* (2006.01)
*C08G 63/82* (2006.01)
*C08G 63/89* (2006.01)
*C08G 63/90* (2006.01)

(52) U.S. Cl.
CPC ............ *C08G 63/823* (2013.01); *C07F 5/066* (2013.01); *C07F 5/069* (2013.01); *C08G 63/89* (2013.01); *C08G 63/90* (2013.01)

(58) Field of Classification Search
CPC ........ C07F 5/066; C07F 5/069; C08G 63/823; C08G 63/89; C08G 63/90
See application file for complete search history.

(56) References Cited

U.S. PATENT DOCUMENTS

| 6,143,863 A | 11/2000 | Gruber et al. |
| 6,608,170 B1 | 8/2003 | Coates |
| 2013/0030144 A1 | 1/2013 | Shaver |

FOREIGN PATENT DOCUMENTS

| CN | 1321692 A | 11/2001 |
| EP | 0331448 A2 | 9/1989 |
| WO | 2011082479 A1 | 7/2011 |

OTHER PUBLICATIONS

Maisse-Francois et al "Structural diversity and versatility for organoaluminum complexes supported by mono- and di-anionic aminophenolate bidentate ligands.", Journal of Organometallic Chemistry 696 ( Jan. 1, 2012), pp. 4248-4256.*
Cameron et al., Synthesis and characterization of neutral dialkylaluminium complexes stabilized by salicylaldiminato ligands, and their conversion to monoalkylaluminium cations, Journal of the Chemical Society, Dalton Transaction (Apr. 3, 2001), (9) pp. 1472-1476.
Du et al., Polymerization of Lactide Using Achiral Bis(pyrrolidene) Schiff Base Aluminum Complexes, Macromolecules (Jan. 23, 2009), 42(4) pp. 1058-1066.
Olson et al., Copper (II) Ethylene Polymerization Catalysts: Do They Really Exist? Organometallics (Sep. 2008), (27) pp. 5333-5338.
Zhang et al., Dimethylaluminium aldiminophenolates: synthesis, characterization and ring-opening polymerization behavior towards lactides, Dalton Transactions (Aug. 8, 2012), 41(38) pp. 11587-11596.
Zhong et al., [(salen)Al]-Mediated, Controlled and Stereoselective Ring-Opening Polymerization of Lactide in Solution and without Solvent: Synthesis of Highly Isotactic Polylactide Stereocopolymers from Racemic D,L-Lactide, Angewandte Chemie (Dec. 2, 2002), 114(23) pp. 4692-4695.
Bourissou et al., Controlled Cationic Polymerization of Lactide, Macromolecules (Nov. 2, 2005), 38: (24):9993-9998.

(Continued)

*Primary Examiner* — Ling Choi
*Assistant Examiner* — Gennadiy Mesh

(57) ABSTRACT

A catalysts for poly(lactide) synthesis having the structure of Formula I:

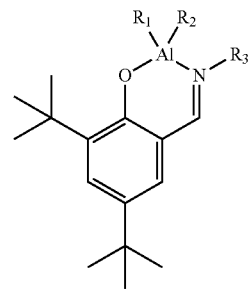

wherein $R_1$ and $R_2$ is, independently, $C_1$-$C_6$ alkoxy, and $R_3$ arylalkyl or substituted phenyl are disclosed. Method of synthesizing the catalysts and method of using the catalysts to prepare poly(lactides) and compositions comprising the catalyst are also disclosed.

8 Claims, 1 Drawing Sheet

(56) References Cited

OTHER PUBLICATIONS

Drumright et al., Polylactic Acid Technology, Advanced Materials (Dec. 1, 2000), 12(23):1841-1846.

Hill et al., Monomeric Group 13 compounds with bidentate (N,O) ligands, Journal of Organometallic Chemistry (May 15, 2001), 628(1):71-75.

Hormnirun et al., Study of ligand substituent effects on the rate and stereoselectivity of lactide polymerization using aluminum salen-type initiators, Proceedings of the National Academy of Sciences of the United States of America (Oct. 17, 2006), 103(42):15343-15348.

International Search Report and Written Opinion for International Application No. PCT/IB2014/059377 mailed on Jan. 6, 2015.

Kubisa, Hyperbranched polyethers by ring-opening polymerization: Contribution of activated monomer mechanism, Journal of Polymer Science Part A: Polymer Chemistry (Feb. 15, 2003), 41(4):457-468.

Penczek, Cationic ring-opening polymerization (CROP) major mechanistic phenomena, Journal of Polymer Science Part A: Polymer Chemistry (Jun. 1, 2000), 38:(11):1919-1933.

Sugimoto et al., Alternating Copolymerization of Carbon Dioxide and Epoxide Catalyzed by an Aluminum Schiff Base-Ammonium Salt system, Journal of Polymer Science; Part A—Polymer Chemistry (Sep. 15, 2005), 43(18):4172-4186.

Baśko et al., Cationic copolymerization of $\epsilon$-caprolactone and L,L-lactide by an activated monomer mechanism, Journal of Polymer Science Part A: Polymer Chemistry (Dec. 15, 2006), 44:7071-7081.

Iwasa et al., Notable effect of imino substituent for the efficient ring-opening polymerization of $\epsilon$-caprolactone initiated by Al complexes containing phenoxy-imine ligand of type, Me 2Al(L) [L: O-2-t Bu6-(RN CH)C 6H 3; R: 2,6-i Pr 2C 6H3, t Bu, adamantyl, C 6F 5], Catalysis Communications (Oct. 30, 2007), 9:1148-1152.

Iwasa et al., Ring-opening polymerization of various cyclic esters by Al complex catalysts containing a series of phenoxy-imine ligands: Effect of the imino substituents for the catalytic activity, Journal of Molecular Catalysis A: Chemical (Jun. 27, 2008), 292:67-75.

Kim et al., Ring-Opening Polymerization of $\epsilon$-Caprolactone by Poly(ethylene glycol) by an Activated Monomer Mechanism, Macromolecular Rapid Communications (2005), 26:643-648.

S. Kaihara et al., "Synthesis of poly(L-lactide) and polyglycolide by ring-opening polymerization," Nature Protocols 2, pp. 2767-2771 (Nov. 1, 2007) [Abstract].

* cited by examiner

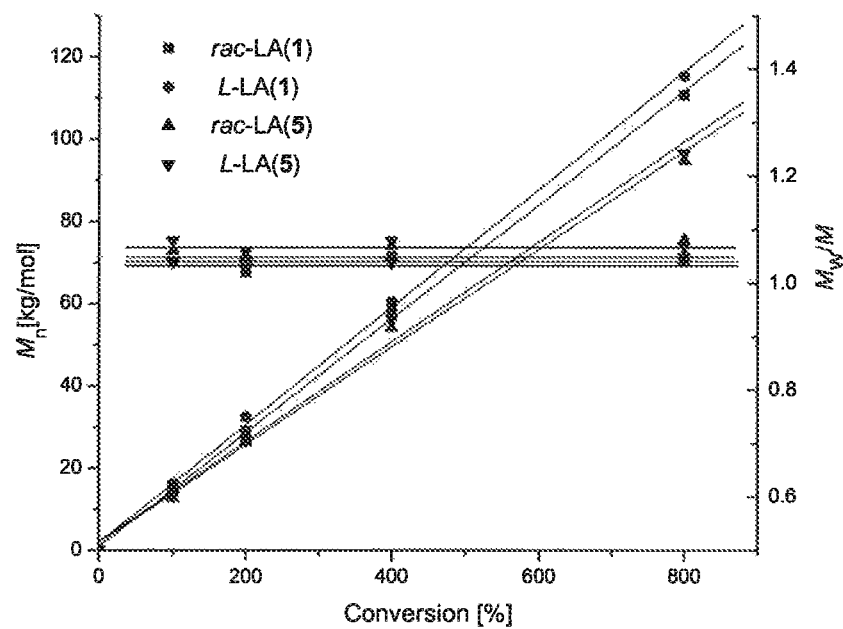

CATALYST FOR POLY(LACTIDE) SYNTHESIS AND USES THEREOF

CROSS-REFERENCE TO RELATED APPLICATIONS

This application is a U.S. National Stage filing under 35 U.S.C. § 371 of International Application No. PCT/IB2014/059377 entitled "Catalysts For Poly(Lactide) Synthesis and Uses Thereof," filed on Mar. 3, 2014, which claims priority from Indian Patent Application Serial No. 1338/CHE/2013, filed on Mar. 26, 2013, and titled "Catalysts for Poly (Lactide) Synthesis and Uses Thereof". The contents of each of these applications are incorporated herein by reference in their entireties.

FIELD

Catalysts for poly(lactide) synthesis and are provided.

BACKGROUND

Synthetic petrochemical-based polymers have had an industrial impact since the 1940s. Despite the numerous advantages of these materials, two major drawbacks remain to be solved, namely, the use of nonrenewable resources for their production and the ultimate disposal of these large-scale commodity polymers. Due to their unique properties, biodegradable polymers have been considered as alternative environmentally friendly polymers, and the advances achieved over the last 30 years in the synthesis, manufacture, and processing of these materials have given rise to a broad range of practical applications from packaging to more sophisticated biomedical devices. Of the variety of biodegradable polymers known, linear aliphatic polyesters are attractive and most used. Notably, these polymers are not only biodegradable (the aliphatic polyester backbone is intrinsically sensitive to water and heat) but also bioassimilable, since their hydrolysis in physiological media gives nontoxic components that are eliminated via the Krebs cycle as water and carbon dioxide.

One of many methods in synthesizing these polymers is the ring opening polymerization of the corresponding cyclic lactone monomers or lactide (LA). Many catalyst systems have been evaluated for the polymerization of lactide and lactones including complexes of aluminum, zinc, tin, and lanthanides. Even strong bases such as metal alkoxides have been used with some success. Tin compounds, especially tin(II) bis-2-ethylhexanoic acid (tin octoate), are used for bulk polymerization due to their solubility in molten state, high catalytic activity, and low rate of racemization of the polymer. Conversions of >90% and less than 1% racemization can be obtained while providing polymer with high molecular weight. The polymerization of lactide and lactones using tin octoate is generally thought to occur via a coordination-insertion mechanism. High molecular weight polymer, good reaction rate, and low levels of racemization are observed with tin octoate catalyzed polymerization. Typical conditions for polymerization are temperatures in a range of 180±210° C., catalyst tin octoate concentrations in a range of 100±1000 ppm, and reaction times in a range of 2±5 hours to reach about 95% conversion. The polymerization is first order in both catalyst and monomer. Frequently hydroxyl-containing initiators such as 1-octanol are used to control molecular weight as well as to accelerate the reaction. One issue in commercialization is the catalyst residue. In spite of the versatile applications of Lewis acids in organic synthesis, their use in polymer chemistry has been quite limited. Certain catalysts have been used, but a major hurdle regarding the commercialization of such processes using certain catalysts is the difficulty in removing catalyst residues and the cytotoxicity associated with such residues, which limit the use of these polymers in biomedical applications.

Accordingly, there is a need for new catalysts that have environmentally benign metals that are constituents in the mammalian anatomy so that the residues are harmless. The embodiments described herein fulfill this need as well as others. The embodiments described herein in are based upon, in part, the synthesis of poly(lactide) (PLA) using mild Lewis acids as catalysts.

SUMMARY

Embodiments described herein provide compounds having the structure of Formula I:

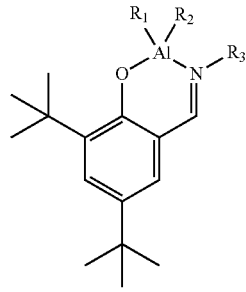

I, wherein $R_1$ is optionally substituted $C_1$-$C_6$ alkyl or optionally substituted $C_1$-$C_6$ alkoxy;

$R_2$ is optionally substituted $C_1$-$C_6$ alkyl or optionally substituted $C_1$-$C_6$ alkoxy;

$R_3$ is optionally substituted tert-butyl,

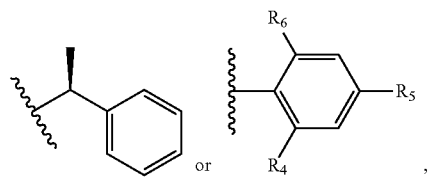

wherein, $R_4$ is selected from the group consisting of H, $C_1$-$C_6$ alkoxy, and $C_1$-$C_6$ alkyl;

$R_5$ is selected from the group consisting of H, $C_1$-$C_6$ alkoxy, and $C_1$-$C_6$ alkyl; and $R_6$ is selected from the group consisting of H, $C_1$-$C_6$ alkoxy, and $C_1$-$C_6$ alkyl.

Methods of preparing poly(lactides) are also provided. In some embodiments, the methods contacting a lactide with a compound having a structure of Formula I:

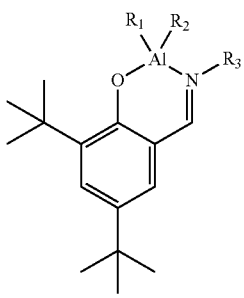

under conditions sufficient to form the poly(lactide), wherein $R_1$ is optionally substituted $C_1$-$C_6$ alkyl or optionally substituted $C_1$-$C_6$ alkoxy;

$R_2$ is optionally substituted $C_1$-$C_6$ alkyl or optionally substituted $C_1$-$C_6$ alkoxy;

$R_3$ is optionally substituted tert-butyl,

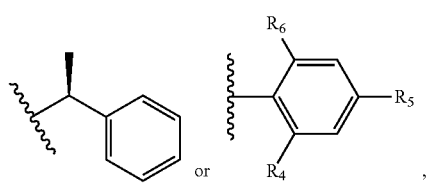

wherein, $R_4$ is selected from the group consisting of H, $C_1$-$C_6$ alkoxy, and $C_1$-$C_6$ alkyl;

$R_5$ is selected from the group consisting of H, $C_1$-$C_6$ alkoxy, and $C_1$-$C_6$ alkyl; and $R_6$ is selected from the group consisting of H, $C_1$-$C_6$ alkoxy, and $C_1$-$C_6$ alkyl. In some embodiments, the method further comprises isolating the poly(lactides).

Methods of preparing certain compounds are also provided. In some embodiments, methods of preparing a compound having the structure of Formula

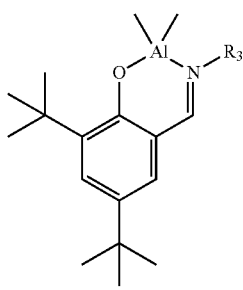

are provided.

In some embodiments, methods of preparing a compound having the structure of Formula III

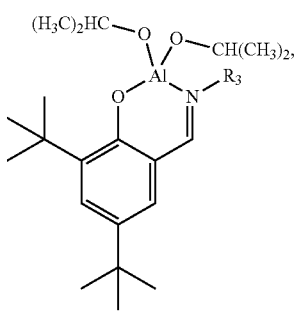

are provided.

Embodiments disclosed herein also provide poly(lactides) prepared according to methods described herein.

Embodiments described herein also provide compositions comprising a compound having Formula I

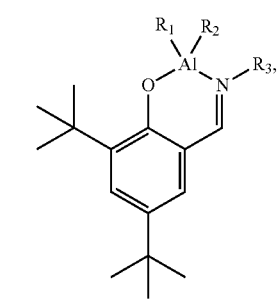

wherein $R_1$ is optionally substituted $C_1$-$C_6$ alkyl or optionally substituted $C_1$-$C_6$ alkoxy;

$R_2$ is optionally substituted $C_1$-$C_6$ alkyl or optionally substituted $C_1$-$C_6$ alkoxy;

$R_3$ is optionally substituted tert-butyl,

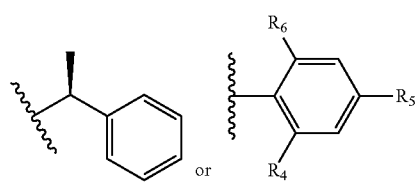

wherein, $R_4$ is selected from the group consisting of H, $C_1$-$C_6$ alkoxy, and $C_1$-$C_6$ alkyl;

$R_5$ is selected from the group consisting of H, $C_1$-$C_6$ alkoxy, and $C_1$-$C_6$ alkyl; and $R_6$ is selected from the group consisting of H, $C_1$-$C_6$ alkoxy, and $C_1$-$C_6$ alkyl. In some embodiments, the composition is a suture, a vascular stent, a packaging material, an engineered tissue, a bone replacement, a drug delivery system, or a biodegradable polymer.

BRIEF DESCRIPTION OF DRAWINGS

FIG. 1 is a plot of conversion vs. molecular weights and molecular distribution with Compounds 1 and 5.

DETAILED DESCRIPTION

This description is not limited to the particular processes, compositions, or methodologies described, as these may vary. The terminology used in the description is for the purpose of describing the particular versions or embodiments only, and it is not intended to limit the scope of the embodiments described herein. Unless defined otherwise, all technical and scientific terms used herein have the same meanings as commonly understood by one of ordinary skill in the art. In some cases, terms with commonly understood meanings are defined herein for clarity and/or for ready reference, and the inclusion of such definitions herein should not necessarily be construed to represent a substantial difference over what is generally understood in the art. However, in case of conflict, the patent specification, including definitions, will prevail.

It must also be noted that as used herein and in the appended claims, the singular forms "a", "an", and "the" include plural reference unless the context clearly dictates otherwise.

As used in this document, terms "comprise," "have," and "include" and their conjugates, as used herein, mean "including but not limited to." While various compositions, methods, and devices are described in terms of "comprising" various components or steps (interpreted as meaning "including, but not limited to"), the compositions, methods, and devices can also "consist essentially of" or "consist of" the various components and steps, and such terminology should be interpreted as defining essentially closed-member groups.

As used herein, the term "alkenyl" means a straight or branched alkyl group having one or more carbon-carbon double bonds and 2-20 carbon atoms, including, but not limited to, ethenyl, 1-propenyl, 2-propenyl, 2-methyl-1-propenyl, 1-butenyl, 2-butenyl, and the like. In some embodiments, the alkenyl chain is from 2 to 10 carbon atoms in length, from 2 to 8 carbon atoms in length, from 2 to 6 carbon atoms in length, or from 2 to 4 carbon atoms in length.

The term "alkoxy" refers to an alkyl group optionally substituted, that is bonded through an oxygen atom. For example, the term "alkoxy" means a straight or branched —O-alkyl group of 1 to 20 carbon atoms, including, but not limited to, methoxy, ethoxy, n-propoxy, isopropoxy, t-butoxy, and the like. In some embodiments, the alkoxy chain is from 1 to 10 carbon atoms in length, from 1 to 8 carbon atoms in length, from 1 to 6 carbon atoms in length, from 1 to 4 carbon atoms in length, from 2 to 10 carbon atoms in length, from 2 to 8 carbon atoms in length, from 2 to 6 carbon atoms in length, or from 2 to 4 carbon atoms in length.

As used herein, the term "alkyl" means a saturated hydrocarbon group which is straight-chained or branched. An alkyl group can contain from 1 to 20, from 2 to 20, from 1 to 10, from 2 to 10, from 1 to 8, from 2 to 8, from 1 to 6, from 2 to 6, from 1 to 4, from 2 to 4, from 1 to 3, or 1, 2 or 3 carbon atoms. Examples of alkyl groups include, but are not limited to, methyl (Me), ethyl (Et), propyl (e.g., n-propyl and isopropyl), butyl (e.g., n-butyl, t-butyl, isobutyl), pentyl (e.g., n-pentyl, isopentyl, neopentyl), hexyl, isohexyl, heptyl, 4,4 dimethylpentyl, octyl, 2,2,4-trimethylpentyl, nonyl, decyl, undecyl, dodecyl, 2-methyl-1-propyl, 2-methyl-2-propyl, 2-methyl-1-butyl, 3-methyl-1-butyl, 2-methyl-3-butyl, 2-methyl-1-pentyl, 2,2-dimethyl-1-propyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl, 2-ethyl-1-butyl, and the like.

As used herein, the term "alkynyl" means a straight or branched alkyl group having one or more triple carbon-carbon bonds and 2-20 carbon atoms, including, but not limited to, acetylene, 1-propylene, 2-propylene, and the like. In some embodiments, the alkynyl chain is 2 to 10 carbon atoms in length, from 2 to 8 carbon atoms in length, from 2 to 6 carbon atoms in length, or from 2 to 4 carbon atoms in length. These can also be optionally substituted.

As used herein, the term "aryl" means a monocyclic, bicyclic, or polycyclic (e.g., having 2, 3 or 4 fused rings) aromatic hydrocarbons. In some embodiments, aryl groups have from 5 to 20 ring atoms or from 5 to 10 ring atoms. Ring atoms can be all C or may contain 1 or more of N, O, and S as replacements for C. Examples of aryl groups include, but are not limited to, phenyl, naphthyl, anthracenyl, phenanthrenyl, indanyl, indenyl, tetrahydronaphthyl, and the like.

Examples of aryl and heteroaryl groups include, but are not limited to:

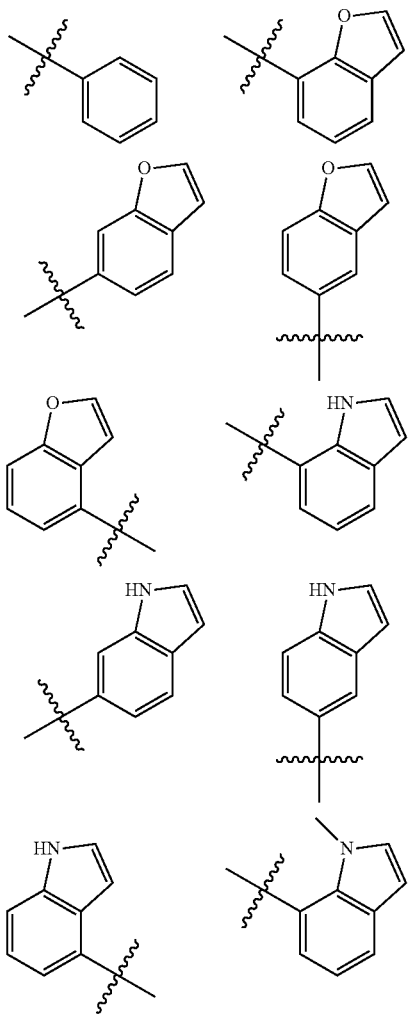

-continued
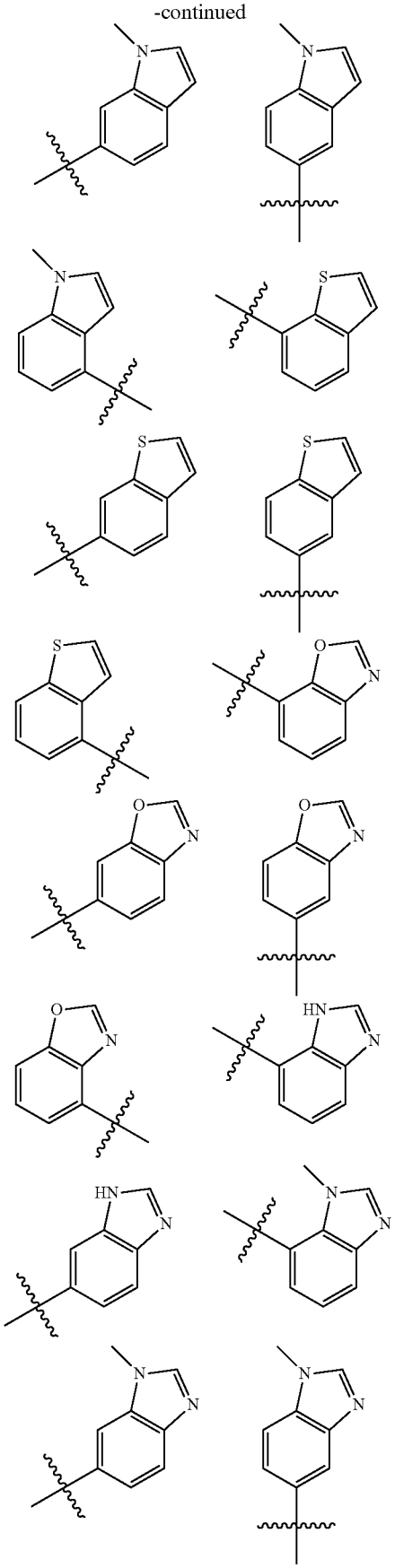
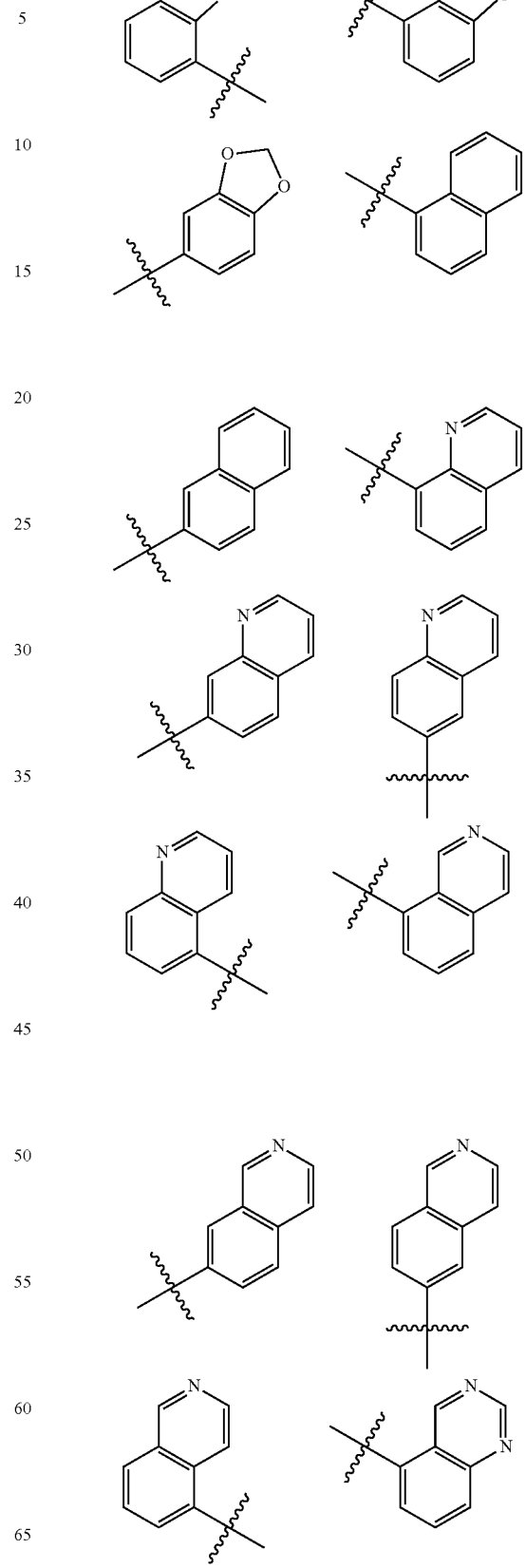

-continued
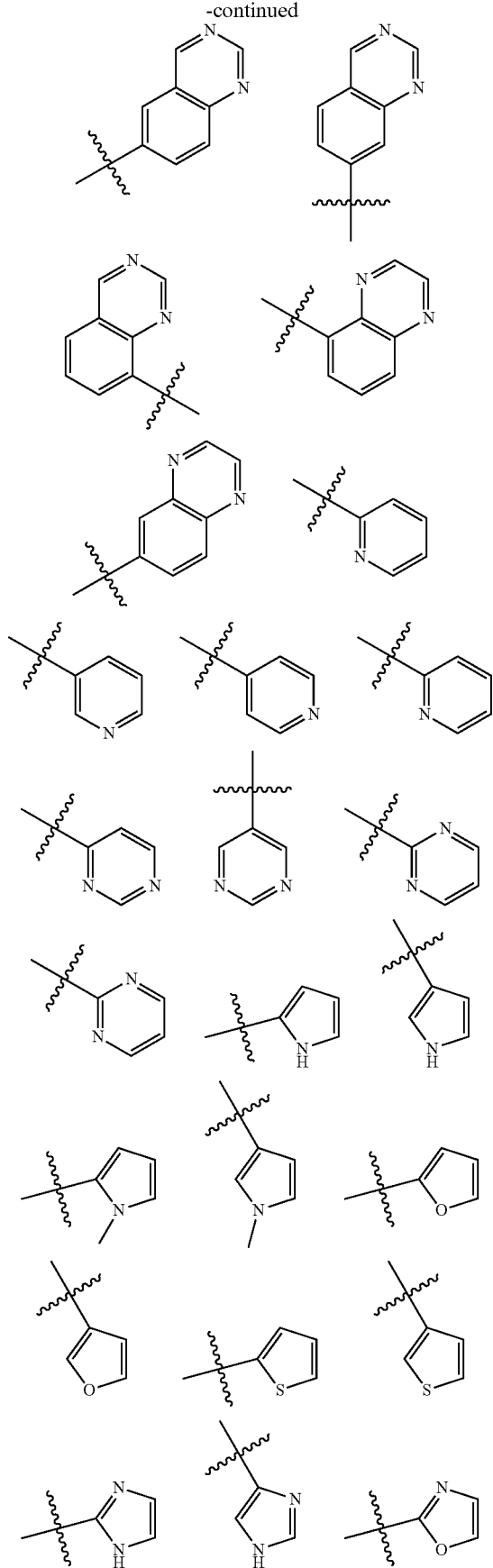
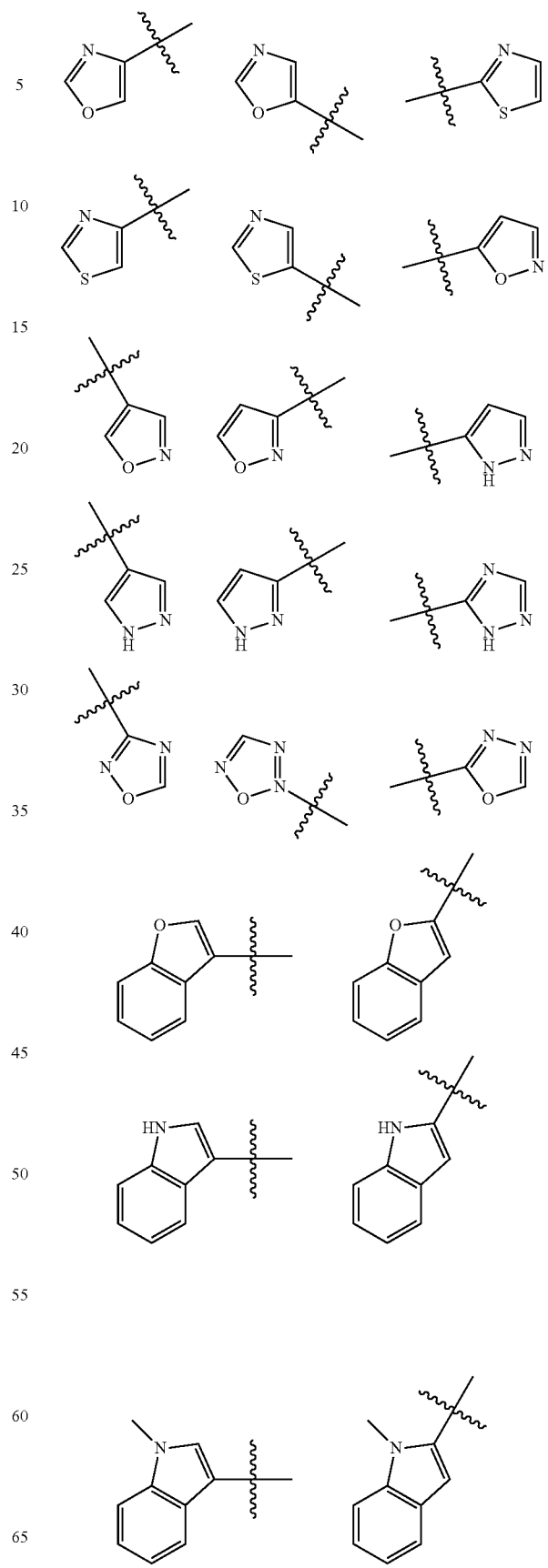

-continued

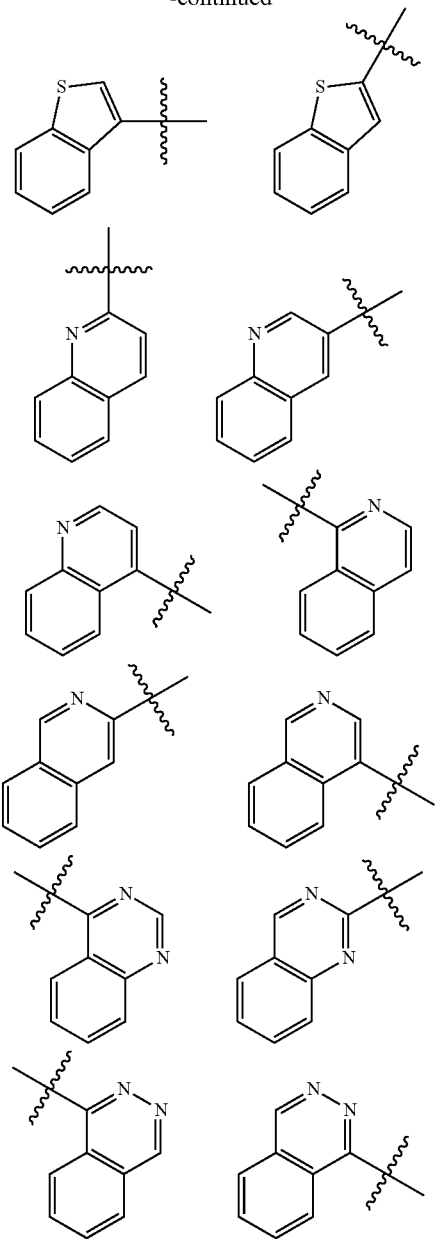

As used herein, the term "arylalkyl" means a $C_{1-6}$alkyl substituted by aryl.

As used herein, the term "contacting" means bringing together of two elements in a system or chemical reaction.

As used herein, the term "cycloalkyl" means non-aromatic cyclic hydrocarbons including cyclized alkyl, alkenyl, and alkynyl groups that contain up to 20 ring-forming carbon atoms. Cycloalkyl groups can include mono- or polycyclic ring systems such as fused ring systems, bridged ring systems, and spiro ring systems. In some embodiments, polycyclic ring systems include 2, 3, or 4 fused rings. A cycloalkyl group can contain from 3 to 15, from 3 to 10, from 3 to 8, from 3 to 6, from 4 to 6, from 3 to 5, or 5 or 6 ring-forming carbon atoms. Ring-forming carbon atoms of a cycloalkyl group can be optionally substituted by oxo or sulfido. Examples of cycloalkyl groups include, but are not limited to, cyclopropyl, cyclobutyl, cyclopentyl, cyclohexyl, cycloheptyl, cyclooctyl, cyclononyl, cyclopentenyl, cyclo-hexenyl, cyclohexadienyl, cycloheptatrienyl, norbornyl, norpinyl, norcarnyl, adamantyl, and the like. Also included in the definition of cycloalkyl are moieties that have one or more aromatic rings fused (having a bond in common with) to the cycloalkyl ring, for example, benzo or thienyl derivatives of pentane, pentene, hexane, and the like (e.g., 2,3-dihydro-1H-inden-1-yl, or 1H-inden-2(3H)-one-1-yl).

As used herein, the term "cycloalkylalkyl" means a $C_{1-6}$alkyl substituted by cycloalkyl.

As used herein, the term "halo" means halogen groups including, but not limited to fluoro, chloro, bromo, and iodo.

As used herein, the term "haloalkyl" means a $C_{1-6}$alkyl group having one or more halogen substituents. Examples of haloalkyl groups include, but are not limited to, $CF_3$, $C_2F_5$, $CHF_2$, $CCl_3$, $CHCl_2$, $C_2Cl_5$, $CH_2CF_3$, and the like.

As used herein, the term "heteroaryl" means an aromatic heterocycle having up to 20 ring-forming atoms (e.g., C) and having at least one heteroatom ring member (ring-forming atom) such as sulfur, oxygen, or nitrogen. In some embodiments, the heteroaryl group has at least one or more heteroatom ring-forming atoms, each of which are, independently, sulfur, oxygen, or nitrogen. In some embodiments, the heteroaryl group has from 3 to 20 ring-forming atoms, from 3 to 10 ring-forming atoms, from 3 to 6 ring-forming atoms, or from 3 to 5 ring-forming atoms. In some embodiments, the heteroaryl group contains 2 to 14 carbon atoms, from 2 to 7 carbon atoms, or 5 or 6 carbon atoms. In some embodiments, the heteroaryl group has 1 to 4 heteroatoms, 1 to 3 heteroatoms, or 1 or 2 heteroatoms. Heteroaryl groups include monocyclic and polycyclic (e.g., having 2, 3 or 4 fused rings) systems. Examples of heteroaryl groups include, but are not limited to, pyridyl, pyrimidinyl, pyrazinyl, pyridazinyl, triazinyl, furyl, quinolyl, isoquinolyl, thienyl, imidazolyl, thiazolyl, indolyl (such as indol-3-yl), pyrryl, oxazolyl, benzofuryl, benzothienyl, benzthiazolyl, isoxazolyl, pyrazolyl, triazolyl, tetrazolyl, indazolyl, 1,2,4-thiadiazolyl, isothiazolyl, benzothienyl, purinyl, carbazolyl, benzimidazolyl, indolinyl, pyranyl, oxadiazolyl, isoxazolyl, triazolyl, thianthrenyl, pyrazolyl, indolizinyl, isoindolyl, isobenzofuranyl, benzoxazolyl, xanthenyl, 2H-pyrrolyl, pyrrolyl, 3H-indolyl, 4H-quinolizinyl, phthalazinyl, naphthyridinyl, quinazolinyl, phenanthridinyl, acridinyl, perimidinyl, phenanthrolinyl, phenazinyl, isothiazolyl, phenothiazinyl, isoxazolyl, furazanyl, phenoxazinyl groups, and the like. Suitable heteroaryl groups include 1,2,3-triazole, 1,2,4-triazole, 5-amino-1,2,4-triazole, imidazole, oxazole, isoxazole, 1,2,3-oxadiazole, 1,2,4-oxadiazole, 3-amino-1,2,4-oxadiazole, 1,2,5-oxadiazole, 1,3,4-oxadiazole, pyridine, and 2-aminopyridine.

As used herein, the term "heteroarylalkyl" means a $C_{1-6}$alkyl group substituted by a heteroaryl group.

As used herein, the term "hydroxy" or "hydroxyl" means an —OH group.

As used herein, the phrase "integer from X to Y" means any integer that includes the endpoints. For example, the phrase "integer from X to Y" means 1, 2, 3, 4, or 5.

As used herein, the phrase "optionally substituted" means that substitution is optional and therefore includes both unsubstituted and substituted atoms and moieties. A "substituted" atom or moiety indicates that any hydrogen on the designated atom or moiety can be replaced with a selection from the indicated substituent groups, provided that the normal valency of the designated atom or moiety is not exceeded, and that the substitution results in a stable compound. For example, if a methyl group is optionally substituted, then 3 hydrogen atoms on the carbon atom can be replaced with substituent groups. Examples of substituents that can be used when a group or atom is substituted are provided herein.

As used herein, the term "phenyl" means —$C_6H_5$. A phenyl group can be unsubstituted or substituted with one, two, or three suitable substituents.

As used herein, the phrase "substantially isolated" means a compound that is at least partially or substantially separated from the environment in which it is formed or detected.

As used herein, the phrase "suitable substituent" or "substituent" means a group that does not nullify the synthetic utility of the compounds described herein or the intermediates useful for preparing them. Examples of suitable substituents that can be used to optionally substitute an atom or group include, but are not limited to: $C_1$-$C_6$alkyl, $C_1$-$C_6$alkenyl, $C_1$-$C_6$alkynyl, $C_5$-$C_6$aryl, $C_1$-$C_6$alkoxy, $C_3$-$C_5$heteroaryl, $C_3$-$C_6$cycloalkyl, $C_5$-$C_6$aryloxy, —CN, —OH, oxo, halo, haloalkyl, —$NO_2$, —$CO_2H$, —$NH_2$, —$NH(C_1$-$C_8$alkyl), —$N(C_1$-$C_8$alkyl)_2$, —$NH(C_6$aryl), —$N(C_5$-$C_6$aryl)_2$, —CHO, —$CO(C_1$-$C_6$alkyl), —$CO((C_5$-$C_6)$aryl), —$CO_2((C_1$-$C_6)$alkyl), and —$CO_((C_5$-$C_6)$aryl). One of skill in art can readily choose a suitable substituent based on the stability and synthetic activity of the compounds described herein. In some embodiments, the substituent is halo.

At various places in the present specification, substituents of compounds may be disclosed in groups or in ranges. It is specifically intended that embodiments include each and every individual subcombination of the members of such groups and ranges. For example, the term "$C_{1-6}$alkyl" is specifically intended to individually disclose methyl, ethyl, propyl, $C_4$alkyl, $C_5$alkyl, and $C_6$alkyl as well as the branched versions of each.

It is further appreciated that certain features described herein, which are, for clarity, described in the context of separate embodiments, can also be provided in combination in a single embodiment. Conversely, various features which are, for brevity, described in the context of a single embodiment, can also be provided separately or in any suitable subcombination.

It is understood that the present disclosure encompasses the use, where applicable, of stereoisomers, diastereomers and optical stereoisomers of the compounds described herein, as well as mixtures thereof. Additionally, it is understood that stereoisomers, diastereomers, and optical stereoisomers of the compounds described herein, and mixtures thereof, are within the scope of the disclosure. By way of non-limiting example, the mixture may be a racemate or the mixture may comprise unequal proportions of one particular stereoisomer over the other. Additionally, the compounds can be provided as a substantially pure stereoisomers, diastereomers and optical stereoisomers (such as epimers).

The compounds described herein can be asymmetric (e.g., having one or more stereocenters). All stereoisomers, such as enantiomers and diastereomers, are intended to be included within the scope of the disclosure unless otherwise indicated. Compounds that contain asymmetrically substituted carbon atoms can be isolated in optically active or racemic forms. Methods of preparation of optically active forms from optically active starting materials are known in the art, such as by resolution of racemic mixtures or by stereoselective synthesis. Many geometric isomers of olefins, C=N double bonds, and the like can also be present in the compounds described herein, and all such stable isomers are contemplated in the present invention. Cis and trans geometric isomers of the compounds are also included within the scope of the invention and can be isolated as a mixture of isomers or as separated isomeric forms. Where a compound capable of stereoisomerism or geometric isomerism is designated in its structure or name without reference to specific R/S or cis/trans configurations, it is intended that all such isomers are contemplated.

Resolution of racemic mixtures of compounds can be carried out by any of numerous methods known in the art, including, for example, fractional recrystallization using a chiral resolving acid which is an optically active, salt-forming organic acid. Suitable resolving agents for fractional recrystallization methods include, but are not limited to, optically active acids, such as the D and L forms of tartaric acid, diacetyltartaric acid, dibenzoyltartaric acid, mandelic acid, malic acid, lactic acid, and the various optically active camphorsulfonic acids such as β-camphorsulfonic acid. Other resolving agents suitable for fractional crystallization methods include, but are not limited to, stereoisomerically pure forms of α-methyl benzyl amine (e.g., S and R forms, or diastereomerically pure forms), 2-phenylglycinol, norephedrine, ephedrine, N-methylephedrine, cyclohexylethylamine, 1,2-diaminocyclohexane, and the like. Resolution of racemic mixtures can also be carried out by elution on a column packed with an optically active resolving agent (e.g., dinitrobenzoylphenylglycine). Suitable elution solvent compositions can be determined by one skilled in the art.

Compounds may also include tautomeric forms. Tautomeric forms result from the swapping of a single bond with an adjacent double bond together with the concomitant migration of a proton. Tautomeric forms include prototropic tautomers which are isomeric protonation states having the same empirical formula and total charge. Examples of prototropic tautomers include, but are not limited to, ketone-enol pairs, amide-imidic acid pairs, lactam-lactim pairs, amide-imidic acid pairs, enamine-imine pairs, and annular forms where a proton can occupy two or more positions of a heterocyclic system including, but not limited to, 1H- and 3H-imidazole, 1H-, 2H- and 4H-1,2,4-triazole, 1H- and 2H-isoindole, and 1H- and 2H-pyrazole. Tautomeric forms can be in equilibrium or sterically locked into one form by appropriate substitution.

Compounds also include hydrates and solvates, as well as anhydrous and non-solvated forms.

In some embodiments, the compounds are substantially or completely isolated. Partial separation can include, for example, a composition enriched in the compound(s) described herein. Substantial separation can include compositions containing at least about 50%, at least about 60%, at least about 70%, at least about 80%, at least about 90%, at least about 95%, at least about 97%, or at least about 99% by weight of the compound, or salt thereof. Methods for isolating compounds and their salts are routine in the art.

Embodiments of various compounds are provided. Where a variable is not specifically recited, the variable can be any option described herein, except as otherwise noted or dictated by context.

In some embodiments, a compound having Formula I:

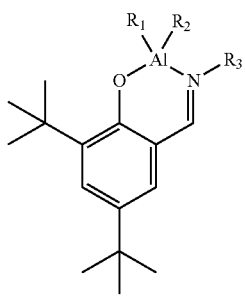

wherein:
R₁ is optionally substituted C₁-C₆ alkyl or optionally substituted C₁-C₆ alkoxy;
R₂ is optionally substituted C₁-C₆ alkyl or optionally substituted C₁-C₆ alkoxy;
R₃ is optionally substituted tert-butyl,

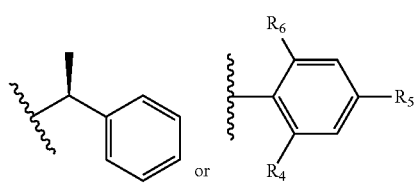

wherein,
R₄ is selected from the group consisting of H, C₁-C₆ alkoxy, and C₁-C₆ alkyl;
R₅ is selected from the group consisting of H, C₁-C₆ alkoxy, and C₁-C₆ alkyl; and
R₆ is selected from the group consisting of H, C₁-C₆ alkoxy, and C₁-C₆ alkyl is provided.
In some embodiments, R₃ is optionally substituted tert-butyl. In some embodiments, R₃ is tert-butyl
In some embodiments, R₃ is

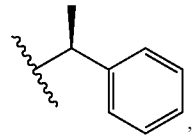 [SMILES: *[C@@H](C)c1ccccc1]

In some embodiments, R₃ is

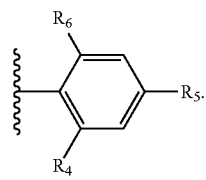

In some embodiments, R₄ is —OCH(CH₃)₂, R₆ is —OCH(CH₃)₂, and R₅ is H.
In some embodiments, R₄ is C₁-C₆ alkyl, R₅ is C₁-C₆ alkyl, and R₆ is C₁-C₆ alkyl.
In some embodiments, R₄ is —CH₃, R₅ is —CH₃, and R₆ is —CH₃.

In some embodiments for a compound of Formula I, R₆ is —OCH(CH₃)₂ and R₂ is —OCH(CH₃)₂. In some embodiments, R₁ is optionally substituted C₁-C₆ alkyl and R₂ is optionally substituted C₁-C₆ alkyl. In some embodiments, R₁ and R₂ are —CH₃.

In some embodiments, the compound is selected from a group consisting of:

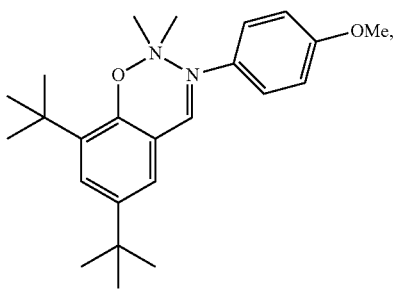

1

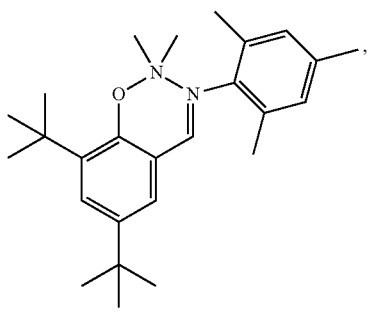

2

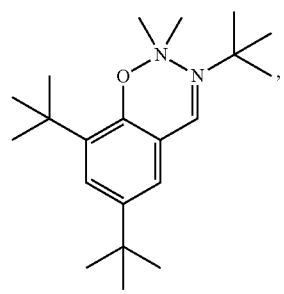

3

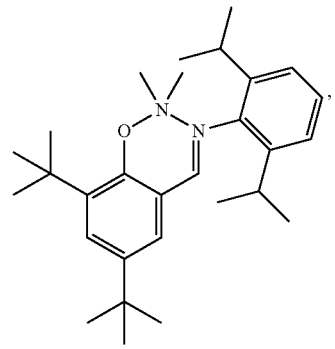

4

5
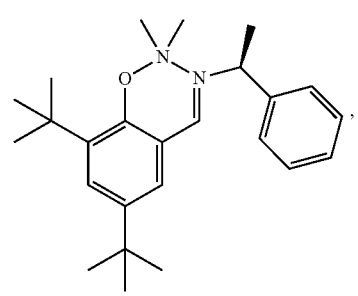
6
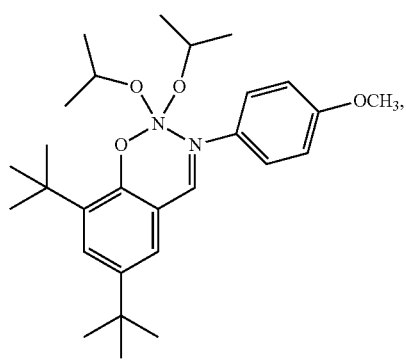
7
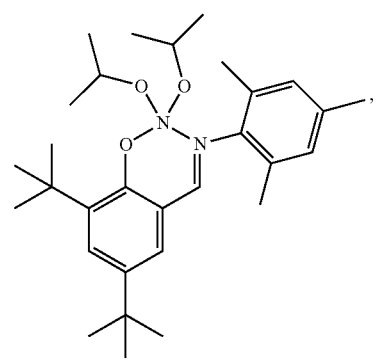
8
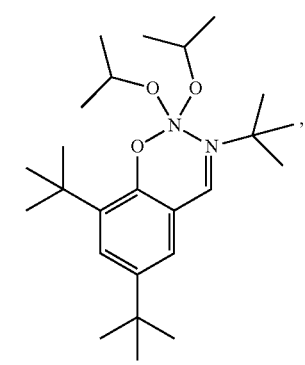
9
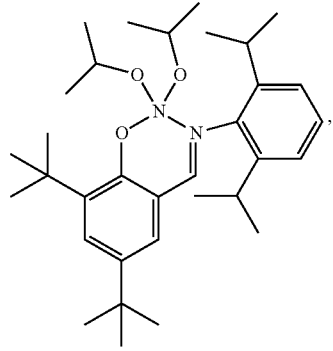
10
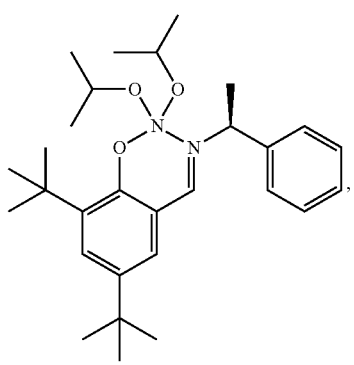
10a
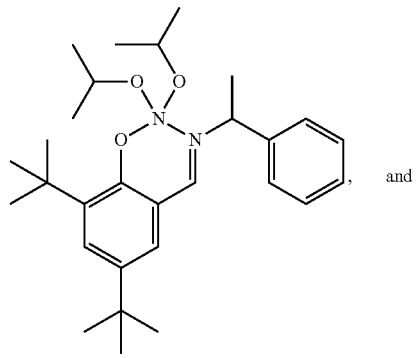
, and
10b
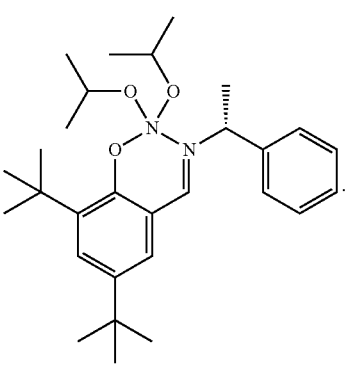
In some embodiments, methods of preparing poly(lactides) are provided. In some embodiments, the method comprises contacting a lactide with a compound having a structure of Formula I:

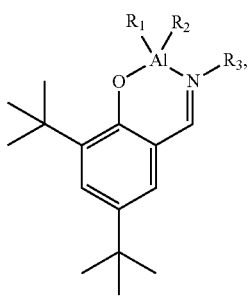

under conditions sufficient to form the poly(lactide), wherein:

$R_1$ is optionally substituted $C_1$-$C_6$ alkyl or optionally substituted $C_1$-$C_6$ alkoxy;

$R_2$ is optionally substituted $C_1$-$C_6$ alkyl or optionally substituted $C_1$-$C_6$ alkoxy;

$R_3$ is optionally substituted tert-butyl,

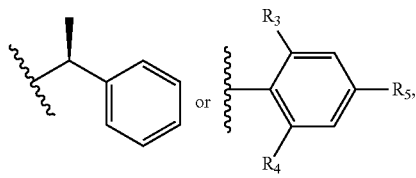

wherein, $R_4$ is selected from the group consisting of H, $C_1$-$C_6$ alkoxy, and $C_1$-$C_6$ alkyl;

$R_5$ is selected from the group consisting of H, $C_1$-$C_6$ alkoxy, and $C_1$-$C_6$ alkyl; and $R_6$ is selected from the group consisting of H, $C_1$-$C_6$ alkoxy, and $C_1$-$C_6$ alkyl.

In some embodiments of the methods, $R_3$ is optionally substituted tert-butyl.

In some embodiments, $R_3$ is tert-butyl. In some embodiments, $R_3$ is

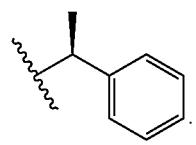

In some embodiments, $R_3$ is

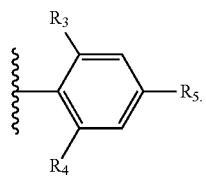

In some embodiments, $R_4$ is —OCH(CH$_3$)$_2$, $R_6$ is —OCH(CH$_3$)$_2$, and $R_5$ is H.

In some embodiments, $R_4$ is $C_1$-$C_6$ alkyl, $R_5$ is $C_1$-$C_6$ alkyl, and $R_6$ is $C_1$-$C_6$ alkyl.

In some embodiments, $R_4$ is —CH$_3$, $R_5$ is —CH$_3$, and $R_6$ is —CH$_3$.

In some embodiments, $R_1$ is —OCH(CH$_3$)$_2$ and $R_2$ is —OCH(CH$_3$)$_2$.

In some embodiments, $R_1$ is optionally substituted $C_1$-$C_6$ alkyl and $R_2$ is optionally substituted $C_1$-$C_6$ alkyl.

In some embodiments, $R_1$ is —CH$_3$ and $R_2$ are —CH$_3$.

In some embodiments, the lactide is rac-lactide or L-lactide.

In some embodiments, the method is performed free of solvents. Examples of solvents that may not be used include, but are not limited to THF, dioxane, DMF, DMS20 and MeCN.

In some embodiments, the ratio of the lactide to a compound of Formula I is at least 50:1, at least 100:1, at least 200:1, at least 300:1, at least 400:1, at least 500:1, at least at least 600:1, at least 700:1, or at least 800:1 (mol/mol). In some embodiments, the ratio of the lactide to a compound of Formula I is from about 50:1 to about 800:1, from about 100:1 to about 800:1, from about 200:1 to about 800:1, from about 300:1 to about 800:1, from about 400:1 to about 800:1, from about 500:1 to about 800:1, from about 600:1 to about 800:1, or from about 700:1 to about 800:1. In some embodiments, the ratio of the lactide to a compound of Formula I is from about 50:1 to about 700:1, from about 50:1 to about 600:1, from about 50:1 to about 500:1, from about 50:1 to about 400:1, from about 50:1 to about 300:1, from about 50:1 to about 200:1, or from about 50:1 to about 100:1.

In some embodiments, the lactide and the compound of Formula I are mixed together. In some embodiments, the lactide and the compound of Formula I are mixed together in an autoclave reactor under an inert atmosphere. In some embodiments, the lactide and the compound of Formula I are at a temperature of about 100-150° C. In some embodiments, the lactide and the compound of Formula I are at a temperature of about 110-150° C. In some embodiments, the lactide and the compound of Formula I are at a temperature of about 120-150° C. In some embodiments, the lactide and the compound of Formula I are at a temperature of about 130-150° C. In some embodiments, the lactide and the compound of Formula I are at a temperature of about 140-150° C.

In some embodiments, the method comprises isolating the poly(lactide). The poly(lactide) can be isolated in any manner that is suitable. In some embodiments, isolating the poly(lactide) comprises filtering, drying, or filtering and drying the poly(lactide). The poly(lactide) can be filtered or dried using any suitable filtering or drying method. The particular filtering or drying method is not critical.

The compounds of Formula I can be prepared by any suitable method or synthetic route. Embodiments provided herein that detail specific synthetic routes are for illustrative purposes only and other routes can be used.

In some embodiments, methods of preparing a compound having Formula II:

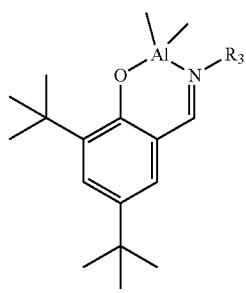

are provided, wherein:
$R_3$ is optionally substituted tert-butyl,

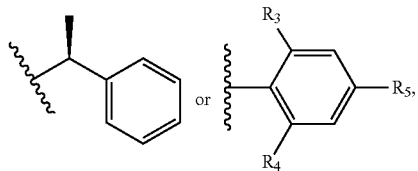

wherein,
$R_4$ is selected from the group consisting of H, optionally substituted $C_1$-$C_6$ alkoxy, and optionally substituted $C_1$-$C_6$ alkyl;
$R_5$ is selected from the group consisting of H, optionally substituted $C_1$-$C_6$ alkoxy, and optionally substituted $C_1$-$C_6$ alkyl; and
$R_6$ is selected from the group consisting of H, optionally substituted $C_1$-$C_6$ alkoxy, and optionally substituted $C_1$-$C_6$ alkyl. In some embodiments, the optional substitution is a halo group.

In some embodiments, the methods comprises contacting a compound having Formula IIa,

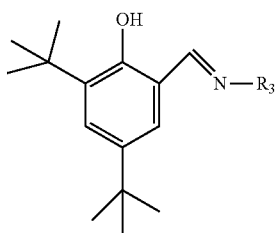

with Me$_3$Al to yield a compound having the structure of Formula II.
wherein: $R_3$ is optionally substituted tert-butyl,

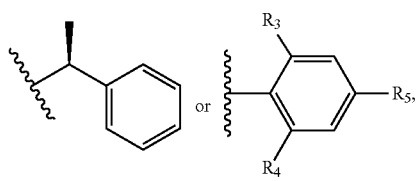

wherein,
$R_4$ is selected from the group consisting of H, optionally substituted $C_1$-$C_6$ alkoxy, and optionally substituted $C_1$-$C_6$alkyl;
$R_5$ is selected from the group consisting of H, optionally substituted $C_1$-$C_6$ alkoxy, and optionally substituted $C_1$-$C_6$ alkyl; and
$R_6$ is selected from the group consisting of H, optionally substituted $C_1$-$C_6$ alkoxy, and optionally substituted $C_1$-$C_6$ alkyl. In some embodiments, the optional substitution is a halo group. Other trialkylaluminum compounds (e.g. Et3Al, i-Pr3Al, and the like) can also be used. If another trialkylaluminum is used the methyl groups connected to the Al atom in Formula II will change to the alkyl groups found in the trialkylaluminum compound used.

In some embodiments, methods of preparing a compound having the structure of Formula III

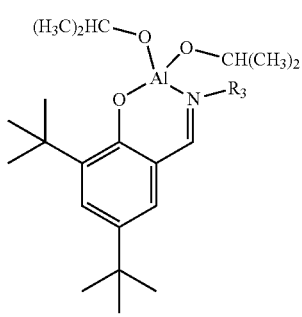

are provided,
wherein: $R_3$ is optionally substituted tert-butyl,

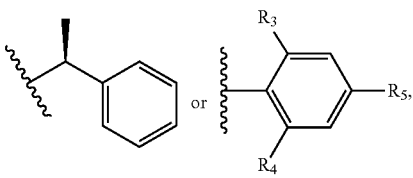

wherein,
$R_4$ is selected from the group consisting of H, optionally substituted $C_1$-$C_6$ alkoxy, and optionally substituted $C_1$-$C_6$ alkyl;
$R_5$ is selected from the group consisting of H, optionally substituted $C_1$-$C_6$ alkoxy, and optionally substituted $C_1$-$C_6$ alkyl; and
$R_6$ is selected from the group consisting of H, optionally substituted $C_1$-$C_6$ alkoxy, and optionally substituted $C_1$-$C_6$ alkyl. In some embodiments, the optional substituent is a halo group.

In some embodiments, the comprises contacting a compound having Formula II

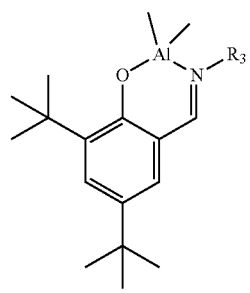

with an alcohol to yield a compound having Formula II. In some embodiments, the alcohol is isopropanol, ethanol, methanol, or any other suitable alcohol.

In some embodiments, a poly(lactide) prepared according to any method described herein are provided.

In some embodiments, compositions comprising a compound of Formula I

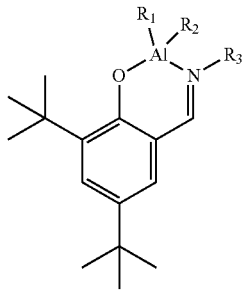

I are provided, wherein:

$R_1$ is optionally substituted $C_1$-$C_6$ alkyl or optionally substituted $C_1$-$C_6$ alkoxy; $R_2$ is optionally substituted $C_1$-$C_6$ alkyl or optionally substituted $C_1$-$C_6$ alkoxy; $R_3$ is optionally substituted tert-butyl,

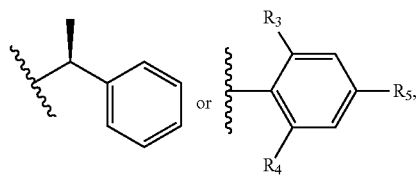

wherein: $R_4$ is selected from the group consisting of H, $C_1$-$C_6$ alkoxy, and $C_1$-$C_6$ alkyl; $R_5$ is selected from the group consisting of H, $C_1$-$C_6$ alkoxy, and $C_1$-$C_6$ alkyl; and $R_5$ is selected from the group consisting of H, $C_1$-$C_6$ alkoxy, and $C_1$-$C_6$ alkyl. In some embodiments, $R_3$ is optionally substituted tert-butyl.

In some embodiments, $R_3$ is

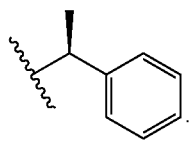

In some embodiments, $R_3$ is

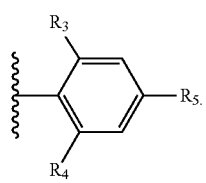

In some embodiments, $R_3$ is

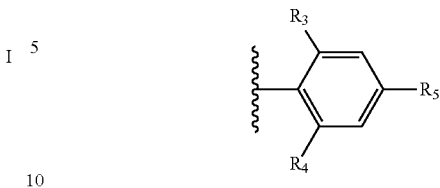

and $R_4$ is —OCH(CH$_3$)$_2$, $R_6$ is —OCH(CH$_3$)$_2$, and $R_5$ is H. In some embodiments, $R_4$ is $C_1$-$C_6$ alkyl, $R_6$ is $C_1$-$C_6$ alkyl, and $R_6$ is $C_1$-$C_6$ alkyl. In some embodiments, $R_4$ is —CH$_3$, $R_5$ is —CH$_3$, and $R_6$ is —CH$_3$.

In some embodiments, where the compound has Formula I, $R_1$ is —OCH(CH$_3$)$_2$ and $R_2$ is —OCH(CH$_3$)$_2$. In some embodiments, $R_1$ is optionally substituted $C_1$-$C_6$ alkyl and $R_2$ is optionally substituted $C_1$-$C_6$ alkyl. In some embodiments, $R_1$ and $R_2$ are —CH$_3$.

In some embodiments, a composition comprising a polylactide and a compound having Formula I are provided. In some embodiments, the composition is a bone replacement with biodegradable materials, a drug delivery system that is suitable for use in the body, a packaging material, a bioengineered tissue, a suture, a stent (e.g. vascular stent), or a biodegradable polymer. The poly(lactides) made using the compounds described herein can be utilized for a variety of systems, devices and purposes. Therefore, in some embodiments, a stent comprising a compound having Formula I is provided. In some embodiments, a synthetic tissue comprising a compound of Formula I is also provided. In some embodiments, a packaging material that can be biodegradable comprises a compound of Formula I is provided. In some embodiments, a suture comprising a compound of Formula I is provided. In some embodiments, a synthetic biodegradable polymer comprising a compound of Formula I is provided. Methods of making the compositions described above are known and, thus, specific details on how to make such compositions are not needed. The compositions described herein will be present in the compositions because they are used to make the poly(lactide) and thus, in some embodiments, some will remain in the polylactide even after polymerization and/or purification of the polymerized poly(lactide). Therefore, when the poly(lactides) are incorporated into various devices and compositions the compounds having Formula I will be present.

In order that the embodiments disclosed herein may be more efficiently understood, examples are provided below. It should be understood that these examples are for illustrative purposes only and are not to be construed as limiting the embodiments in any manner.

EXAMPLES

Example 1: Materials and Methods

All the reactions were performed under a dry argon atmosphere using standard Schlenk techniques or glove box techniques with the rigorous exclusion of moisture and air. Toluene was dried by heating under refluxing condition for 6 hours over sodium and benzophenone and distilled fresh prior to use. CDCl$_3$ used for NMR spectral measurements was dried over calcium hydride for 48 hours, distilled and stored in a glove box. 1H and 13C NMR spectra were recorded with a Bruker Avance 400 instrument. Chemical shifts for 1H and 13C NMR spectra were referenced to residual solvent resonances and are reported as parts per million relative to SiMe$_4$. ESI-MS spectra of the samples were recorded using Waters Q-Tof micro mass spectrometer. MALDI-TOF measurements were performed on a Bruker Daltonics instrument in dihydroxy benzoic acid matrix. Elemental analyses were performed with a Perkin Elmer Series 11 analyzer.

Molecular weights (Mn) and the polydispersity indices (MWDs) of the polymer samples produced by the ROP of LA were determined by using a GPC instrument with Waters 510 pump and Waters 410 differential refractometer as the detector. Three columns, WATERS STRYGEL-HR5, STRYGEL-HR4 and STRYGEL-HR3 each of dimensions (7.8× 300 mm) were serially connected one after another. Measurements were done in THF at 27° C. for all the cases. Measurement of number average molecular weights (Mn), weight average molecular weights (Mw) and polydispersity (Mw/Mn) (MWDs) of the polymers were performed relative to polystyrene standards.

All the raw materials for the synthesis of the compounds and the compounds described below were purchased from Sigma-Aldrich and used without further purification. rac-LA and L-LA were purchased from Sigma-Aldrich. rac-LA and L-LA were sublimed under argon atmosphere and stored in a glove box.

Example 2: Synthesis of Compound 1

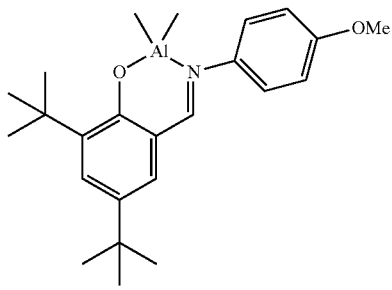

1

In a glove box, trimethyl aluminum (21.23 mg, 0.30 mmol) was added to a stirred solution of 2,4-tert-butyl-6-((4-methoxyphenylimino)methyl)phenol (100 mg, 0.30 mmol) in 5 ml toluene. The reaction mixture was stirred for 24 hours. The solvent was evaporated under reduced pressure to give a yellow solid. The product was crystallized from toluene, recovered by filtration and dried under vacuum. Yield: 112.20 mg (97%); M.P. 180° C. 1H NMR (CDCl3, 400 MHz, ppm): δ=8.28 (s, CH=N, 1H, e), 7.58 (d, Ar—H, 1H, $^4J_{HH}$=2.8 Hz, m2'), 7.28 (d, Ar—H, 1H, $^4J_{HH}$=2.1 Hz, m2), 7.10 (d, Ar—H, 2H, $^3J_{HH}$=2.4 Hz, o1), 6.98 (d, Ar—H, 2H, $^3J_{HH}$=8 Hz, m1), 3.88 (s, OCH3, 3H, d), 1.44 (s, C(CH3)3, 9H, c), 1.32 (s, C(CH3)3, 9 H, b), −0.74 (s, CH3, 6H, a); 13C NMR (100 MHz, CDCl3, ppm): δ=169.64 (Ar—CH=N), 162.16 (Ar-Cp1), 158.98 (Ar-Ci2), 140.74 (Ar—Ci1), 139.33 (Ar-Cp2), 132.76 (Ar—Co2'), 129.21 (Ar—Cm2'), 123.35 (Ar—Cm2), 123.35 (Ar—Co1), 118.80 (Ar—Co2), 115.51 (Ar—Cm1), 56.34 (Ar—OCH-3), 35.44 (CMe3), 34.21 (CMe3), 31.43 (CMe3), 29.41 (CMe3), −9.18 (CH3).

Example 3: Synthesis of Compound 2

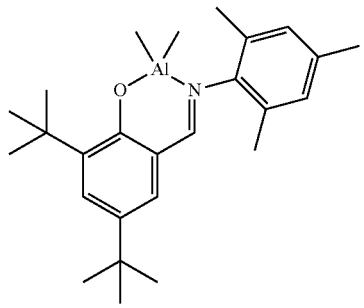

2

2,4-di-tert-butyl-6-((mesitylimino)methyl)phenol (100 mg, 0.28 mmol) and trimethyl aluminium (21 mg, 0.28 mmol) were reacted according to the procedure used for the synthesis of Compound 1. Yield: 110.85 mg (96%); M.P. 195° C. 1H NMR (CDCl3, 400 MHz, ppm)): δ=8.02 (s, CH=N, 1H, f), 7.64 (d, Ar—H, 2H, $^4J_{HH}$=2.4 Hz, m2), 7.01 (d, Ar—H, 2H, $^4J_{HH}$=2.8 Hz, m1), 2.31 (s, Ar—CH3, 3H, e), 2.20 (s, Ar—CH3, 6H, d), 1.50 (s, C(CH3)3, 9H, c), 1.34 (s, C(CH3)3, 9H, b) −0.80 (s, CH3, 6H, a); 13C NMR (100 MHz, CDCl3, ppm): δ=167.77 (Ar—CH=N, h), 162.59 (Ar-Ci1), 160.72, (Ar-Ci2), 139.08 (Ar-Cp2), 136.77, (Ar—Co2') 131.52, (Ar—Co1), 129.60 (Ar—Co1), 128.96 (Ar—Cm1), 128.50 (Ar-Cp1), 126.66 (Ar—Cm2), 118.40 (Ar—Co2), 35.49 (CMe3, g), 34.21 (CMe3, f), 31.64 (CMe3, e), 29.60 (CMe3, d) 20.99 (Ar—CH3, c) 18.69 (Ar—CH3, b) −8.84 (CH3, a).

Example 4: Synthesis of Compound 3

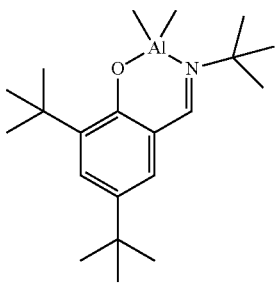

3

2,4-di-tert-butyl-6-((tert-butylimino)methyl)phenol (100 mg, 0.35 mmol) and trimethyl aluminium (24.9 mg, 0.35 mmol) were reacted according to the procedure for the synthesis of Compound 1. Yield: 114.75 mg (96%); M.P. 175° C. 1H NMR (CDCl3, 400 MHz, ppm): δ=8.26 (s, CH=N, 1H, e), 7.51 (d, Ar—H, 1H, $^4J_{HH}$=2.8 Hz, m1'), 6.99 (d, Ar—H, 1H, $^4J_{HH}$=2.8 Hz, m1), 1.50 (s, C(CH3)3, 9H, d), 1.41 (s, C(CH3)3, 9H, c), 1.31 (s, NC(CH3)3, 9H, b) −0.71 (s, CH3, 6H, a); 13C NMR (100 MHz, CDCl3, ppm): δ=169.19 (Ar—CH=N, h), 161.29 (Ar-Ci), 140.32 (Ar-Cp1), 138.73 (Ar—Co1'), 131.64 (Ar—Cm1'), 128.94 (Ar—Co1), 118.47 (Ar—Cm1), 59.69 (CMe3-N=CH, g), 35.33 (CMe3, f), 34.17 (CMe3, e), 31.51 (CMe3, d), 30.38 (CMe3, c), 29.39 (CMe3, b) −6.96 (CH3, a).

Example 5: Synthesis of Compound 4

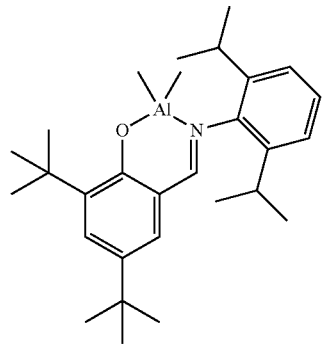

4

2,4-di-tert-butyl-6-((2,6-diisopropylphenylimino)methyl) phenol (100 mg, 0.25 mmol) and trimethyl aluminium (18.3 mg, 0.25 mmol) were reacted according to the procedure for the synthesis of Compound 1. Yield: 110.50 mg (97%); M.P. 195° C. 1H NMR (CDCl3, 400 MHz, ppm): δ=8.01 (s, CH=N, 1H, f), 7.59 (d, Ar—H, 2H, $^4J_{HH}$=2.4 Hz, m2), 7.21 (s, Ar—H, 1H, p1), 6.94 (d, 2H, $^4J_{HH}$=2.8 Hz, m1), 3.04-3.08 (m, Me$_2$CH, 2H, e), 1.43 (s, C(CH$_3$)$_3$, 9H, d), 1.23-1.26 (m, CH(CH$_3$)2, 12H, c), 1.06 (s, C(CH$_3$)$_3$ 9H, b), −0.84 (s, CH$_3$, 6H, a); 13C NMR (100 MHz, CDCl3, ppm): δ=174.00 (Ar—CH=N, h), 162.68 (Ar—O, Ci2), 142.76 (Ar—O, Ci1), 142.23 (Ar-Cp2), 140.97 (Ar—Co1), 139.25 (Ar—Co2'), 133.18 (Ar—Cm2'), 128.87 (Ar—Cm2), 128.09 (Ar—Cm1), 124.32 (Ar-Cp1), 118.00 (Ar—Co2), 35.52 (CMe$_3$, g), 34.22 (CMe$_3$ f), 31.39 (CMe$_3$, e), 29.48 (CMe$_3$, d), 28.23 (CHMe$_2$, c), 22.78 (CHMe$_2$, b), −9.41 (CH$_3$, a).

Example 6: Synthesis of Compound 5

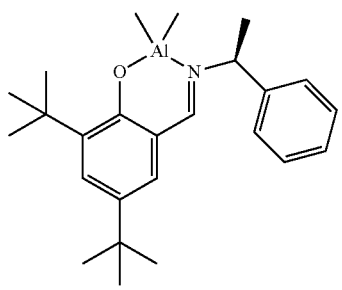

5

2,4-di-tert-butyl-6-((1-phenylethylamino)methyl)phenol (100 mg, 0.30 mmol) and trimethyl aluminium (21.4 mg, 0.30 mmol) were reacted according to the procedure for the synthesis of Compound 1. Yield: 114.25 mg (98%); M.P. 178° C. 1H NMR (CDCl3, 400 MHz, ppm)): δ=7.99 (s, CH=N, 1H, g), 7.38 (d, Ar—H, H, $^4J_{HH}$=2.8 Hz, m2'), 7.22-7.28 (m, Ar—H, 5H, o1, m1, m2), 6.78 (d, Ar—H, 1H, $^4J_{HH}$=2.8 Hz, p1), 4.78-4.84 (m, CH, 1H, f), 1.66 (d, 3H, CH$_3$, 3H, e), 1.27 (s, C(CH$_3$)$_3$, 9H, d), 1.15 (s C(CH$_3$)$_3$, 9H, c), −0.91 (s, CH$_3$ 3H, b), −1.04 (s, CH$_3$, 3H, a); 13C NMR (100 MHz, CDCl3, ppm): δ=171.01 (Ar—CH=N, j), 161.67 (Ar—O, Ci2), 140.53 (Ar—O, Ci1), 140.04 (Ar-Cp2), 138.87 (Ar-Co2'), 127.97-131.95 (Ar—Co2, Co1, Cp1, Cm1, Cm2'), 118.41 (Ar—Cm2), 63.58 (CH, h), 35.39 (CMe$_3$, g), 34.17 (CMe$_3$ f), 31.47 (CMe$_3$, e), 29.41 (CMe$_3$, d), 21.17 (CH$_3$, c), −8.76 (CH$_3$, b), −9.20 (CH$_3$, a).

Example 7: Synthesis of Compound 6

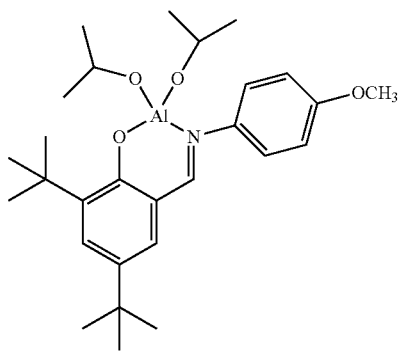

6

In a glove box, propan-2-ol (30.39 mg, 0.50 mmol) was added to a stirred solution of Compound 1 (100 mg, 0.25 mmol) in 5 ml toluene. The reaction mixture was stirred for 24 hours. The solvent was evaporated under reduced pressure to give a pale yellow solid. The product was crystallized from toluene, recovered by filtration and dried under vacuum. Yield: 118.25 mg (97%); M.P. 165° C. 1H NMR (CDCl3, 400 MHz, ppm): δ=8.28 (s, CH=N, 1H, f), 7.66 (d, Ar—H, 1H, $^4J_{HH}$=2.8 Hz, m2'), 7.33 (d, Ar—H, 1H, $^4J_{HH}$=2.4 Hz, m2), 7.18 (d, Ar—H, 2H, $^3J_{HH}$=2.4 Hz, m1), 7.01 (d. Ar—H, 2H, $^3J_{HH}$=2 Hz, o1), 4.06-4.09 (m, CH(CH$_3$)$_2$, 2H, e), 3.76-3.78 (m, OCH$_3$, 3H, d), 1.40 (s, C(CH$_3$)$_3$, 9H, c), 1.36 (s, C(CH$_3$)$_3$, 9H, b), 1.13 (s, CH$_3$, 12H, a); 13C NMR (100 MHz, CDCl3, ppm): δ=167.91 (Ar—CH=N, h), 158.45 (Ar-Cp1), 144.17 (Ar-Ci2), 139.89 (Ar-Ci1), 138.76 (Ar-Cp2), 130.20 (Ar—Co2'), 129.19 (Ar—Cm2'), 125.67 (Ar—Cm2), 123.59 (Ar—Co1), 120.03 (Ar—Co2), 113.63 (Ar—Cm1), 62.94 (CH(CH$_3$)$_2$, g), 55.67 (Ar—OCH$_3$), 35.39 (CMe$_3$), 34.94 (CMe$_3$), 31.53 (CMe$_3$), 29.62 (CMe$_3$), 27.96 (CH(CH$_3$)$_2$).

Example 8: Synthesis of Compound 7

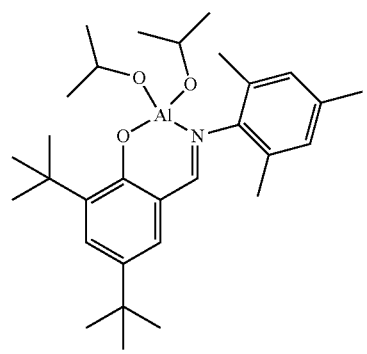

7

Compound 2 (100 mg, 0.24 mmol) and, propan-2-ol (30 mg, 0.49 mmol) were reacted according to the procedure for the synthesis of Compound 6. Yield: 115.75 mg (95%); M.P. 175° C. 1H NMR (CDCl3, 400 MHz, ppm)): δ=8.27 (s, CH=N, 1H, g), 7.58 (d, Ar—H, 1H, $^4J_{HH}$=2.8 Hz, m2'), 7.44 (d, Ar—H, 1H, $^4J_{HH}$=2.8 Hz, m2), 6.94 (d, Ar—H, 2H, m1), 4.01-4.09 (m, CH(CH$_3$)$_2$, 2H, f), 2.31 (s, Ar—CH$_3$, 3H, e), 2.19 (s, Ar—CH$_3$, 6H, d), 1.50 (s, C(CH$_3$)$_3$, 9H, c), 1.39 (s, C(CH$_3$)$_3$, 9H, b) 1.19 (d, CH(CH$_3$)$_2$, 12H, J$_{HH}$=4, a); 13C NMR (100 MHz, CDCl3, ppm): δ=167.77 (Ar—CH=N, j), 163.66 (Ar-Ci1), 158.58 (Ar-Ci2), 140.49 (Ar-Cp2), 137.22, (Ar—Co2') 132.38, (Ar—Co1), 129.77 (Ar—Co1), 129.09 (Ar—Cm1), 128.49 (Ar-Cp1), 126.67 (Ar—Cm2), 118.59 (Ar—Co2), 63.46 (CH(CH$_3$)$_2$, h), 35.44 (CMe$_3$, g), 34.34 (CMe$_3$, f), 31.64 (CMe$_3$, e), 29.61 (CMe$_3$, d) 27.30 (CH(CH$_3$)$_2$, c) 20.93 (Ar—CH$_3$, b) 19.00 (Ar—CH$_3$, a).

Example 9: Synthesis of Compound 8

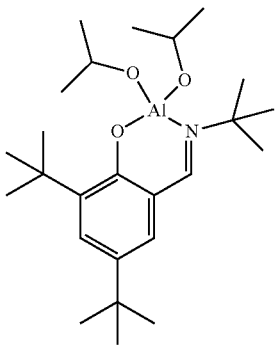

8

Compound 3 (100 mg, 0.29 mmol) and propan-2-ol (34.8 mg, 0.58 mmol) were reacted according to the procedure for the synthesis of Compound 6. Yield: 116.45 mg (93%); M.P. 167° C. 1H NMR (CDCl3, 400 MHz, ppm): δ=8.36 (s, CH=N, 1H, f), 7.56 (d, Ar—H, 1H, $^4J_{HH}$=2.4 Hz, m1'), 7.06 (d, Ar—H, 1H, $^4J_{HH}$=2.4 Hz, m1), 4.16-4.19 (m, CH(CH$_3$)$_2$, 2H, e), 1.51 (s, C(CH$_3$)$_3$, 9H, d), 1.42 (s, C(CH$_3$)$_3$, 9H, c), 1.33 (s, N(CH$_3$)$_3$, 9H, b) 1.15 (d, CH(CH$_3$)$_2$, 12H, J$_{HH}$=6, a); 13C NMR (100 MHz, CDCl3, ppm): δ=170.44 (Ar—CH=N, j), 161.43 (Ar-Ci), 140.47 (Ar-Cp1), 138.75 (Ar—Co1'), 131.70 (Ar—Cm1'), 128.77 (Ar—Co1), 118.33 (Ar—Cm1), 63.39 (CH(CH$_3$H), h), 59.89 (CMe$_3$-N=CH, g), 35.14 (CMe$_3$, f), 34.31 (CMe$_3$, e), 31.31 (CMe$_3$, d), 30.19 (CMe$_3$, c), 29.39 (CMe$_3$, b) 27.69 (CH(CH$_3$)$_2$, a).

Example 10: Synthesis of Compound 9

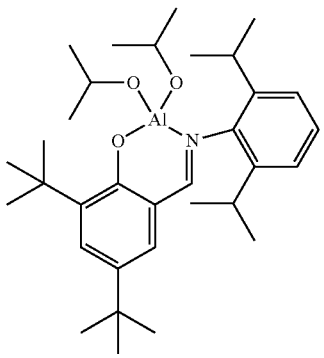

9

Compound 4 (100 mg, 0.22 mmol) and propan-2-ol (26.7 mg, 0.44 mmol) were reacted according to the procedure for the synthesis of Compound 6. Yield: 114.60 mg (96%); M.P. 182° C. 1H NMR (CDCl3, 400 MHz, ppm): δ=8.07 (s, CH=N, 1H, f), 7.59 (d, Ar—H, 1H, $^4J_{HH}$=2.4 Hz, m2'), 7.13-7.26 (m, Ar—H, 2H, p1, m2), 6.94 (d, 2H, $^4J_{HH}$=2.4 Hz, m1), 4.06-4.09 (m, CH(CH$_3$)$_2$, 2H, e), 3.27-3.30 (m, Me$_2$CH, 2H, d), 1.44 (s, C(CH$_3$)$_3$, 9H, c), 1.30 (s, C(CH$_3$)$_3$ 9H, b), 1.11-1.20 (m, CH(CH$_3$)$_2$, 24H, a, a'); 13C NMR (100 MHz, CDCl13, ppm): δ=167.68 (Ar—CH=N, j), 158.60 (Ar—O, Ci2), 146.56 (Ar—O, Ci1), 140.63 (Ar-Cp2), 139.04 (Ar—Co1), 137.32 (Ar—Co2'), 129.20 (Ar—Cm2'), 128.39 (Ar—Cm2), 125.46 (Ar—Cm1), 123.32 (Ar-Cp1), 117.90 (Ar—Co2), 65.51 (CH(CH$_3$)$_2$, h), 35.35 (CMe$_3$, g), 34.37 (CMe$_3$ f), 31.38 (CMe$_3$, e), 29.65 (CMe$_3$, d), 28.20 (CHMe$_2$, c), 25.70 (CHMe$_2$, b), 23.78 (CH(CH$_3$)$_2$, a).

Example 11: Synthesis of Compound 10

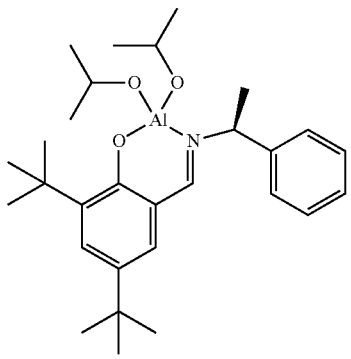

10

Compound 5 (100 mg, 0.25 mmol) and propan-2-ol (30.5 mg, 0.51 mmol) were reacted according to the procedure for the synthesis of Compound 6. Yield: 119.20 mg (97%); M.P. 170° C. 1H NMR (CDCl3, 400 MHz, ppm)): δ=7.99 (s, CH=N, 1H, g), 7.38 (d. Ar—H, H, $^4J_{HH}$=2.8 Hz, m2'), 7.22-7.28 (m, Ar—H, 5H, o1, m1, m2), 6.78 (d, Ar—H, 1H, $^4J_{HH}$=2.8 Hz, p1), 4.78-4.84 (m, CH, 1H, f), 1.66 (d, 3H, CH$_3$, 3H, e), 1.27 (s, C(CH$_3$)$_3$, 9H, d), 1.15 (s C(CH)$_3$, 9H, c), −0.91 (s, CH$_3$ 3H, b), −1.04 (s, CH$_3$, 3H, a); 13C NMR (100 MHz, CDCl3, ppm): δ=171.01 (Ar—CH=N, j), 161.67 (Ar—O, Ci2), 140.53 (Ar—O, Ci1), 140.04 (Ar-Cp2), 138.87 (Ar—Co2'), 127.97-131.95 (Ar—Co2, Co1, Cp1, Cm1, Cm2'), 118.41 (Ar—Cm2), 63.58 (CH, h), 35.39 (CMe$_3$, g), 34.17 (CMe$_3$ t), 31.47 (CMe$_3$, e), 29.41 (CMe$_3$, d), 21.17 (CH$_3$, c), −8.76 ((CH$_3$, b), −9.20 (CH$_3$, a).

Example 12: Polymerization of poly(lactide)

The polymerizations were performed under bulk solvent-free condition. For L-LA and rac-LA polymerization, 173.4 μmol of catalyst and 5 g L-LA or rac-LA (34.7 mmol) were used during the polymerization. The contents were taken into a 100 mL stainless steel autoclave reactor with mechanical stirring under an argon atmosphere. The steel autoclave was heated to 130° C. The contents were rapidly stirred. The progress of polymerization was monitored by recording the 1H NMR spectra of the reaction mixture periodically. The polymerization was quenched by gradual cooling the autoclave to ambient temperature in almost 30 min and pouring the contents into cold methanol.

The formed polymer was collected by filtration. The filtered product was dried in vacuum until a constant weight was achieved. Single crystals were grown in a glove box at −25° C. from diluted toluene and acetonitrile (few drops) solutions of the respective compounds over a period of 10 days. X-ray Data was collected with a Bruker AXS (Kappa Apex 2) CCD diffractometer equipped with graphite monochromated Mo (Kα) (λ=0.7107 Å) radiation source. The data were collected with 100% completeness for θ up to 25°. ω and φ scans were employed to collect the data. The frame width for ω for was fixed to 0.5° for data collection. The frames were subjected to integration and data were reduced for Lorentz and polarization corrections using SAINT-NT. The multi-scan absorption correction was applied to the data set. All structures were solved using SIR-92 and the refinement was done using SHELXL-97. Location of all the hydrogen atoms could be found in the difference Fourier map. The hydrogen atoms attached to carbon atoms were fixed at chemically meaningful positions and were allowed to ride with the parent atom during refinement.

Compounds 1-10 were found to be potent initiators towards the bulk polymerization of lactides in the absence of solvent to yield PLA. The data is summarized in Table 1.

TABLE 1

Polymerization data for rac-LA and L-LA with 1-10 in the ratio $[M]_0/[Mg]_0 = 200$ at 140° C.

| Entry | Catalyst | Monomer | Time$^a$ (min) | Yield$^b$ (%) | $M_n$ (GPC)$^c$ (kg/mol) | $M_n$ (Theo)$^d$ (kg/mol) | $M_w/M_n$ | $P_r^e$ |
|---|---|---|---|---|---|---|---|---|
| 1 | 1 | rac-LA | 10 | 98 | 29.10 | 29.16 | 1.02 | 0.84 |
| 2 | 2 | rac-LA | 8 | 98 | 26.25 | 29.18 | 1.03 | 0.83 |
| 3 | 3 | rac-LA | 11 | 99 | 25.56 | 29.11 | 1.03 | 0.84 |
| 4 | 4 | rac-LA | 8 | 99 | 29.52 | 29.22 | 1.04 | 0.82 |
| 5 | 5 | rac-LA | 16 | 98 | 26.48 | 29.22 | 1.06 | 0.96 |
| 6 | 6 | rac-LA | 45 | 99 | 26.28 | 29.16 | 1.09 | 0.83 |
| 7 | 7 | rac-LA | 50 | 99 | 25.43 | 29.18 | 1.11 | 0.83 |
| 8 | 8 | rac-LA | 45 | 99 | 26.80 | 29.11 | 1.09 | 0.84 |
| 9 | 9 | rac-LA | 55 | 99 | 26.55 | 29.22 | 1.12 | 0.83 |
| 10 | 10 | rac-LA | 30 | 99 | 25.84 | 29.22 | 1.10 | 0.94 |
| 11 | 1 | L-LA | 12 | 99 | 32.43 | 29.16 | 1.03 | |
| 12 | 2 | L-LA | 12 | 98 | 27.77 | 29.17 | 1.05 | |
| 13 | 3 | L-LA | 15 | 98 | 26.95 | 29.11 | 1.05 | |
| 14 | 4 | L-LA | 10 | 99 | 30.21 | 29.22 | 1.04 | |
| 15 | 5 | L-LA | 17 | 99 | 26.85 | 29.22 | 1.05 | |
| 16 | 6 | L-LA | 40 | 99 | 27.15 | 29.16 | 1.08 | |
| 17 | 7 | L-LA | 50 | 99 | 26.11 | 29.17 | 1.09 | |
| 18 | 8 | L-LA | 50 | 98 | 24.76 | 29.11 | 1.10 | |
| 19 | 9 | L-LA | 60 | 99 | 23.35 | 29.22 | 1.12 | |
| 20 | 10 | L-LA | 40 | 99 | 22.95 | 29.22 | 1.09 | |

$^a$Time of polymerization measured by quenching the polymerization reaction at 100% conversion.
$^b$Isolated yield at 100% conversion.
$^c$Measured by gel permeation chromatography at 27° C. in THF relative to polystyrene standards with Mark-Houwink corrections.
$^d$Theoretical mol wt at 100% conversion.
$^e$Calculated from homonuclear decoupled $^1$H NMR.

Analysis of the results find that the use of the alkoxy compounds (e.g. Compounds 6-10) take longer a time for polymerization of the poly(lactide). The observed molecular weights of the poly(lactide) are in close proximity to the calculated or theoretical weight. The molecular weight distribution of the poly(lactide) in each case is narrow. Polymerization of rac-LA leads to the synthesis of PLA with predominantly heterotactic enchainment. Additionally, presence of chirality in the catalyst increases the stereochemical output.

Example 13: Modification of Catalyst to Lac Affects Polymerization

Studies on the variation of Mn with [M]o/[Mg]o ratio using Compound 1 and Compound 5 (results shown in Table 2 below) indicate that there is a steady increase in the molecular weight with increasing [M]o/[Mg]o ratio. At the same time, the molecular weight distribution remains almost invariant. Here also there is a close proximity between the observed molecular weights and the calculated ones. Similar results were found with Compounds 6 and 10 conclusions were found, respectively.

A plot of conversion vs. molecular weights and molecular distribution with Compounds 1 and 5 (FIG. 1) remains consistent with the fact that these polymerization processes have can be used continually without renewal. Kinetic studies reveal that it is a first order reaction without induction. The apparent rate constants are almost identical.

TABLE 2

Studies on the variations of Mn with $[M]_0/[Mg]_0$ ratio using 1 and 5 at 140° C.

| Catalyst | $[M]_0/[Mg]_0$ | Monomer | Time$^a$ (min) | Yield$^b$ (%) | $M_n$ (GPC)$^c$ (kg/mol) | $M_n$ (Theo)$^d$ (kg/mol) | $M_w/M_n$ |
|---|---|---|---|---|---|---|---|
| 1 | 100 | rac-LA | 5 | 98 | 14.54 | 14.80 | 1.04 |
| 1 | 200 | rac-LA | 10 | 98 | 29.10 | 29.21 | 1.02 |
| 1 | 400 | rac-LA | 30 | 99 | 58.18 | 58.04 | 1.05 |
| 1 | 800 | rac-LA | 80 | 99 | 110.75 | 115.69 | 1.04 |
| 1 | 100 | rac-LA | 6 | 98 | 16.22 | 14.80 | 1.04 |
| 1 | 200 | rac-LA | 12 | 99 | 32.43 | 29.21 | 1.03 |
| 1 | 400 | rac-LA | 28 | 99 | 60.45 | 58.04 | 1.04 |
| 1 | 800 | rac-LA | 75 | 99 | 115.34 | 115.69 | 1.005 |
| 5 | 100 | L-LA | 8 | 99 | 12.82 | 14.81 | 1.08 |
| 5 | 200 | L-LA | 16 | 99 | 26.48 | 29.22 | 1.06 |
| 5 | 400 | L-LA | 30 | 99 | 54.14 | 58.05 | 1.08 |
| 5 | 800 | L-LA | 85 | 99 | 94.65 | 115.71 | 1.07 |
| 5 | 100 | L-LA | 8 | 99 | 13.25 | 14.81 | 1.06 |
| 5 | 200 | L-LA | 17 | 99 | 26.85 | 29.22 | 1.05 |

TABLE 2-continued

Studies on the variations of Mn with $[M]_0/[Mg]_0$ ratio using 1 and 5 at 140° C.

| Catalyst | $[M]_0/$ $[Mg]_0$ | Monomer | Time[a] (min) | Yield[b] (%) | $M_n$ (GPC)[c] (kg/mol) | $M_n$ (Theo)[d] (kg/mol) | $M_w/M_n$ |
|---|---|---|---|---|---|---|---|
| 5 | 400 | L-LA | 28 | 99 | 56.28 | 58.05 | 1.07 |
| 5 | 800 | L-LA | 80 | 99 | 96.55 | 115.71 | 1.08 |

[a]Time of polymerization measured by quenching the polymerization reaction at 100% conversion.
[b]Measured by gel permeation chromatography at 27° C. in THF relative to polystyrene standards with Mark-Houwink corrections.
[c]Theoretical mol wt at 100% conversion.

The results provided herein show that starting with a rac-LA to catalyst ratio 100:1, the Mns and MWDs of the polymers obtained by successive addition of monomer (so that the rac-LA to catalyst ratio remains 200:1, 400:1 and 800:1) give results consistent with what is observed in Table 2. This reveals that the catalyst system has the capability of accommodating monomer feed to a very large extent. Hence, these catalysts can also be referred to as "high mileage catalysts."

Example 14: DSC and TGA Analysis

DSC analyses were performed on TGA Q500 V20 Instrument (TA Instruments; New Castle, Del., USA) under nitrogen atmosphere. The heating and cooling rate was 10° C./min. Ramp method was used for these analysis and 4.2 mg sample was taken to perform of the analysis.

Glass transition ($T_g$) temperatures were visible in the DSC measurement curves as a step in endothermal direction. However, the inflection points of the curve were also correlated to $T_g$. From the plot, $T_g$ was calculated by taking tangents line of the first derivative of first endothermic curve. The total liquefaction point $T_m$ was calculated by applying the same method. Results are indicated in the following table.

TABLE 3

Determination of $T_g$ and $T_m$ values for various catalyst and monomer combinations.

| Entry | Catalyst | Monomer | Intrinsic Viscosity (dl/g) | $T_g$ (° C.) | $T_m$ (° C.) |
|---|---|---|---|---|---|
| 1 | 1 | rac-LA | 2.31654 | 50 | 172 |
| 2 | 2 | rac-LA | 2.24541 | 46 | 171 |
| 3 | 1 | L-LA | 2.39371 | 53 | 172 |
| 4 | 2 | L-LA | 2.28654 | 50 | 171 |
| 5 | 6 | rac-LA | 2.14998 | 45 | 170 |
| 6 | 7 | rac-LA | 2.08846 | 44 | 170 |
| 7 | 6 | L-LA | 2.28178 | 48 | 171 |
| 8 | 7 | L-LA | 2.20686 | 47 | 171 |

All of the catalyst and monomer combinations tested provided good, commercially suitable results. The values obtained for all samples are especially attractive for use of the polymers at high temperatures and extreme conditions. The results also show that the catalysts can be successfully used with various monomers to give equally attractive polymers.

We claim:

1. A compound, having a structure of Formula I:

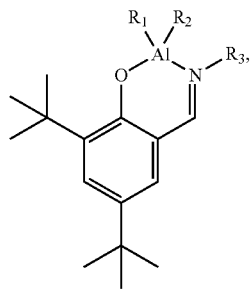

wherein:

$R_1$ is $C_1$-$C_6$ alkoxy;

$R_2$ is $C_1$-$C_6$ alkoxy; and $R_3$ is optionally substituted

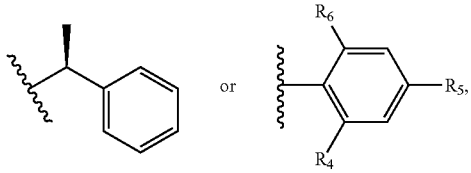

wherein:

$R_4$ is selected from the group consisting of H and $C_1$-$C_6$ alkoxy, $R_5$ is selected from the group consisting of H and $C_1$-$C_6$ alkoxy, and $R_6$ is selected from the group consisting of H and $C_1$-$C_6$ alkoxy.

2. The compound of claim 1, wherein $R_3$ is

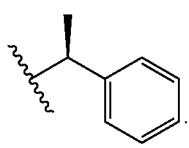 [SMILES: *[C@@H](C)c1ccccc1]

3. The compound of claim 1, wherein $R_3$ is

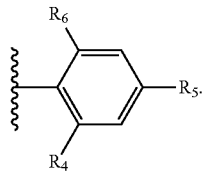

4. The compound of claim 3, wherein $R_4$ is —OCH($CH_3$)$_2$, $R_6$ is —OCH($CH_3$)$_2$, and $R_5$ is H.

5. The compound of claim 1, wherein $R_1$ is —OCH($CH_3$)$_2$ and $R_2$ is —OCH($CH_3$)$_2$.

6. A composition, comprising a compound having Formula I:

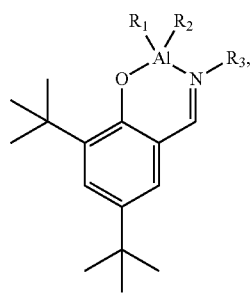

wherein:
$R_1$ is $C_1$-$C_6$ alkoxy;
$R_2$ is $C_1$-$C_6$ alkoxy; and
$R_3$ is optionally substituted

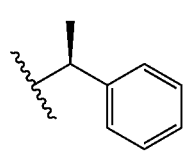 or 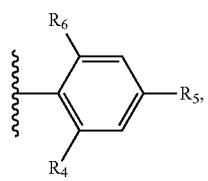

wherein:
$R_4$ is selected from the group consisting of H and $C_1$-$C_6$ alkoxy,
$R_5$ is selected from the group consisting of H and $C_1$-$C_6$ alkoxy, and
$R_6$ is selected from the group consisting of H and $C_1$-$C_6$ alkoxy.

7. A compound, having a structure of Formula I:

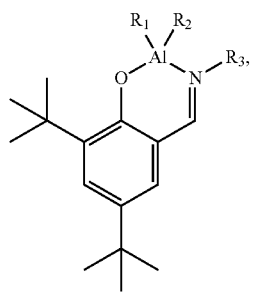

wherein:
$R_1$ is $C_1$-$C_6$ alkoxy;
$R_2$ is $C_1$-$C_6$ alkoxy; and
$R_3$ is optionally substituted

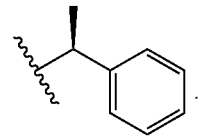

8. A compound, having a structure of Formula I:

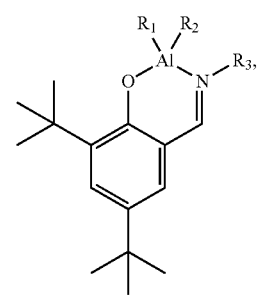

wherein:
$R_1$ is $C_1$-$C_6$ alkoxy;
$R_2$ is $C_1$-$C_6$ alkoxy; and
$R_3$ is optionally substituted

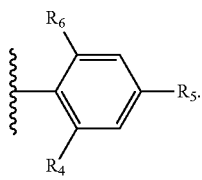

wherein:
$R_4$ is selected from the group consisting of H and $C_1$-$C_6$ alkoxy;
$R_5$ is selected from the group consisting of H and $C_1$-$C_6$ alkoxy; and
$R_6$ is selected from the group consisting of H and $C_1$-$C_6$ alkoxy.

* * * * *